US006330472B2

(12) United States Patent
Sukumar

(10) Patent No.: US 6,330,472 B2
(45) Date of Patent: Dec. 11, 2001

(54) PROPHYLACTIC AND THERAPEUTIC TREATMENT OF THE DUCTAL EPITHELIUM FOR A MAMMARY GLAND FOR CANCER

(75) Inventor: Saraswati Vaidyanathan Sukumar, Columbia, MD (US)

(73) Assignee: Johns Hopkins University School of Medicine, Baltimore, MD (US)

(*) Notice: Subject to any disclaimer, the term of this patent is extended or adjusted under 35 U.S.C. 154(b) by 0 days.

(21) Appl. No.: 09/240,206

(22) Filed: Jan. 29, 1999

Related U.S. Application Data

(60) Continuation of application No. 09/093,145, filed on Jun. 8, 1998, now Pat. No. 6,153,184, which is a division of application No. 08/692,001, filed on Aug. 2, 1996, now Pat. No. 5,763,415.
(60) Provisional application No. 60/028,929, filed on Aug. 3, 1995.

(51) Int. Cl.$^7$ ............................... A61N 1/30; A61K 31/00
(52) U.S. Cl. ........................... 604/21; 514/1; 514/2
(58) Field of Search ........................ 514/2, 1; 424/852; 606/41; 519/212, 427, 59; 604/53, 21; 569/316

(56) References Cited

U.S. PATENT DOCUMENTS

| 4,568,673 | * | 2/1986 | Brooks | 514/178 |
|---|---|---|---|---|
| 4,623,660 | * | 11/1986 | Richardson | 514/514 |
| 5,149,527 | | 9/1992 | Weisenthal | 424/85.2 |
| 5,215,904 | | 6/1993 | Gould et al. | 435/455 |
| 5,236,844 | * | 8/1993 | Basset et al. | 435/320.1 |
| 5,304,489 | | 4/1994 | Rosen | 435/320.1 |
| 5,383,849 | * | 1/1995 | Johlin et al. | 604/53 |
| 5,472,441 | * | 12/1995 | Edwards et al. | 606/41 |
| 5,478,556 | * | 12/1995 | Elliot et al. | 424/852 |
| 5,585,096 | | 12/1996 | Martuza et al. | 424/93.2 |
| 5,651,964 | | 7/1997 | Hung et al. | 424/93.2 |
| 5,662,896 | | 9/1997 | Barber et al. | 424/93.2 |
| 5,744,133 | | 4/1998 | Lathe et al. | 424/93.2 |
| 5,747,469 | | 5/1998 | Roth et al. | 519/44 |
| 5,780,009 | | 7/1998 | Karatzas | 424/9 |
| 5,833,975 | | 11/1998 | Paoletti et al. | 424/93.2 |
| 5,837,693 | | 11/1998 | German et al. | 514/44 |
| 5,858,365 | * | 1/1999 | Faller et al. | 424/184.1 |
| 5,866,550 | | 2/1999 | Frisch | 514/44 |
| 6,096,874 | * | 8/2000 | Wallace et al. | 534/10 |

FOREIGN PATENT DOCUMENTS

| 0 118365 | 9/1984 | (EP) . |
|---|---|---|
| 0 352722 | 1/1990 | (EP) . |
| 0 657174 | 6/1995 | (EP) . |
| WO93/02556 | 2/1993 | (WO) . |
| WO94/09160 | 4/1994 | (WO) . |
| WO94/26915 | 11/1994 | (WO) . |

OTHER PUBLICATIONS

Lukac et al. (Cancerlit Database, AN: 94696782, Non–serial, (1993). CCPC–93: Second International Cancer Chemo Prevention Conference, Apr. 28–30, 1993, Germany), 1993.*
Stedman's Medicat Dictionary, p. 438, col. 2, 1995.*
Dorland's Illustrated Medical Dictionary, p. 425, 1994.*
Berkow et al., The Merck Manual of Diagosis and Therapy, 1992, Merck Research Laboratories, Sixteenth Edition, p. 1818.*
Tannock et al., The Basic Science of Oncology, 1992, McGraw–Hill, Inc., Second Edition, pp. 225–227.*
Ariyama et al. *Medline*, AN: 91185944, International J. Pancreat, 7, 1–3, 37–47, abstract (1990).
Berchem et al., *Cancer Research*, 55:735–738 (Feb. 15, 1995).
Bièche et al., *Cancer Research*, 54:4274–4276 (Aug. 15, 1994).
Chen et al., *Proc. Natl. Acad. Sci. USA*, 91:3054–3057 (Apr. 1994).
Culver et al. "Gene Therapy for Cancer," *TIG*, 10(5): 174–178 (1994).
Friedman. "Gene Therapy of Cancer through Restoration of Tumor–Suppressor Functions?" *Cancer* (supp) 70(6): 1810–1816 (1992).
Frykberg et al., "Overview of the Biology and Management of Ductal Carcinoma in Situ of the Breast," Database *Medline*, File Server Stn Karlsruhe, Abstract 94273121 (1994).
Fujiwara et al., "Gene Therapeutics and Gene Therapy for Cancer," *Current Opinion in Oncology*, 6:96–105 (1994).
Hanby etal., *Proc. Annu. Meet. Am. Assoc. Cancer Res.*, 35:A1085 (1994).
Haran et al., *Cancer Research*, 54:5511–5514 (Nov. 1, 1994).
Hodgson. "Advances in Vector Systems for Gene Therapy," *Exp Opin Ther. Patents*, 5(5): 459–468 (1995).
LaFont et al. "Which Gene for Which Restenosis?" *The Lancet*, 346: 1442–1443 (1995).
Manome et al., *Cancer Research*, 54:5408–5413 (Oct. 15, 1994).
Marshall. "Gene Therapy's Growing Pains," *Science*, 269: 1050–1055 (1995).
Mastrangelo et al. *Seminars in Oncology*, 23(1): 4–21 (1996).

(List continued on next page.)

*Primary Examiner*—Dave T. Nguyen
(74) *Attorney, Agent, or Firm*—Leydig, Voit & Mayer, Ltd.

(57) ABSTRACT

The present invention provides prophylactic and therapeutic methods of treating the ductal epithelium of an exocrine gland, in particular a mammary gland, for disease, in particular cancer. The methods comprise contacting the ductal epithelium of the exocrine gland with an epithelium-destroying agent, preferably by ductal cannulation, so as to realize a prophylactic or therapeutic effect.

18 Claims, 1 Drawing Sheet

OTHER PUBLICATIONS

Miller et al. "Targeted Vectors for Gene Therapy," *FASEB*, vol. 9: 190–199 (1995).

Miyadera et al., *Cancer Reserach*, 55:1687–1690 (Apr. 15, 1995).

Orkin et al. "Report and Recommendations . . . Gene Therapy," *NIHPress*: 1–40 (1995).

Osaki et al., *Cancer Research*, 54:5258–5261 (Oct. 15, 1994).

Pansera, *Medical Hypotheses*, 33:107–111 (1990).

Pitts, *Molecular Carcinogenesis*, 11:127–130 (1994).

Russo et al., "Biology of Disease. Comparative Study of Human and Rat Mammary Tumorigenesis," *Laboratory Investigation*, 62:244–278 (1990).

Tamaki et al., "A Human Monoclonal Antibody Derived from Axillary Lymph Nodes of a Breast Cancer Patient," *Hybridoma*, 8:293–302 (1989).

Tamm et al., "Interleukin 6 Decreases Cell–Cell Association and Increases Motility of Ductal Breast Carcinoma Cells," *The Journal of Experimental Medicine*, 170:1649–1669 (Nov., 1989).

Zenklusen et al., "The Immunohistochemical Reactivity of a New Anti–Epithelial Monoclonal Antibody (MAb b–12) Against Breast Carcinoma and Other Normal and Neoplastic Human Tissues," *Virchows Archiv A Pathological Anatomy and Histopathology*, 413:3–10 (1988).

\* cited by examiner

PROPHYLACTIC AND THERAPEUTIC TREATMENT OF THE DUCTAL EPITHELIUM FOR A MAMMARY GLAND FOR CANCER

This is a continuation of application(s) Ser. No. 09/093,145, filed on Jun. 8, 1998, now U.S. Pat. No. 6,153,184 of which is a divisional of Ser. No. 08/692,001, filed on Aug. 2, 1996, and issued as U.S. Pat. No. 5,763,415 on Jun. 9, 1998, which claims priority to U.S. provisional patent application Ser. No. 60/028,929, filed Aug. 3, 1995.

The invention disclosed in this application was made with government support under NIH planning grant P20 CA/ES66205, "Gene-mediated prevention of Cancer," and grant NIH 1RO1 CA 57993, "Genetic and hormonal factors in mammary carcinogenesis," awarded by the National Institutes of Health, and with support of the American Cancer Society under grant RD388, "Targeted disruption of breast cells: a novel strategy for cancer prevention." Therefore, the government has certain rights in this invention.

TECHNICAL FIELD OF THE INVENTION

The present invention relates to the use of an epithelium-destroying agent to destroy the epithelium of an exocrine gland, particularly the mammary gland, in the prophylactic and therapeutic treatment of disease, in particular cancer.

BACKGROUND OF THE INVENTION

Exocrine glands are glands that release a secretion external to or at the surface of an organ by means of a canal or duct. Examples of exocrine glands include, among others, the mammary glands, prostate, liver, gall bladder, pancreas, kidneys, sweat glands, and salivary glands. Cancers of exocrine glands pose a major health problem, frequently resulting in death. Currently, cancers of the breast and prostate are among the leading causes of death among women and men, respectively.

The mature human breast comprises from six to nine major ducts, which emanate from the nipple, serially branch into ducts and terminate in lobuloalveolar structures (Russo et al., Lab. Invest. 62(3): 244–278 (1990)). This branching network of ducts is composed of epithelial cells in a supporting matrix of connective tissue and endothelial cells.

Tissues removed from the human female breast during surgery and autopsy have been examined in numerous studies directed to the nature and site of origin of neoplastic growth. Subgross sampling and histological confirmation have enabled pathological characterization of entire breasts, leading to the postulation of the existence of four major possible sites of origin of mammary carcinomas, namely ducts, terminal ducts, ductules, and acini (Russo et al., supra). Ductal origin is supported by the presence of more extensive epithelial proliferations, which are presumed to be preneoplastic, in surgically removed cancerous breasts as compared to nonmalignant breasts removed during autopsies (Russo et al., supra).

With a cumulative lifetime risk of a woman developing breast cancer estimated to be 1 in 9, there is an urgent need to develop therapeutic methods of treatment that are more effective, less invasive and accompanied by fewer side effects and prophylactic methods of treatment that are more effective than increased and intensified physical monitoring and far less extreme than radical mastectomy. In spite of the recent discovery of the heritable breast cancer susceptibility loci, BRCA1 (Miki et al., Science 266: 66–71 (1994)) and BRCA2, and other cancer susceptibility loci, and the increasing ability of physicians to identify women with elevated breast cancer risk, prophylactic methods are still currently limited to physical monitoring and prophylactic mastectomy.

In view of the above, it is an object of the present invention to provide a method of locally treating an exocrine gland prophylactically for disease. It is another object of the present invention to provide a method of locally treating an exocrine gland, in particular the mammary gland, prophylactically for cancer. Another object of the present invention is to provide a method of locally treating an exocrine gland therapeutically for disease. Yet another object of the present invention is to provide a method of locally treating a mammary gland therapeutically for cancer. Still yet another object of the present invention is to provide a method of locally treating a mammary gland both therapeutically and prophylactically for cancer. These and other objects and advantages, as well as additional inventive features, will become apparent from the detailed description provided herein.

SUMMARY OF THE INVENTION

The present invention provides prophylactic and therapeutic methods of treating the ductal epithelium of an exocrine gland, in particular the mammary gland, for disease, in particular cancer. The method comprises contacting the ductal epithelium of the exocrine gland, in particular the mammary gland, with an epithelial-destroying agent. The ductal epithelium is preferably contacted with the agent by ductal cannulation. The epithelium-destroying agent is preferably a vector comprising a thymidine kinase gene, which is used in combination with ganciclovir (GCV), which can be systemically administered. Another preferred epithelium-destroying agent is a vector comprising a hypoxanthine phosphoribosyl transferase (HPRT) gene, which is used in combination with hypoxanthine aminopterin thymidine (HAT) nucleotide, which can be systemically administered. Also preferred as an epithelium-destroying agent is a vector comprising a gene, which, upon transformation of a cell of the ductal epithelium and expression therein, induces apoptosis or death of the transformed cell. A preferred apoptosis-inducing gene is bclxs. Other preferred epithelial-destroying agents include a cytolytic virus, such as Vaccinia virus, and ethanol. The preceding methods can additionally comprise contacting the ductal epithelium with a cytokine or hematopoietic growth factor, such as GM-CSF. Also provided by the present invention is a method of treating the ductal epithelium of a mammary gland both therapeutically and prophylactically for cancer. The combined therapeutic/prophylactic method comprises treating the mammary gland therapeutically by surgery, radiation and/or chemotherapy and contacting the ductal epithelium of the mammary gland, either concomitantly or subsequently, with an epithelium-destroying agent, which does not specifically target cancerous cells. The combined therapeutic/prophylactic method can additionally comprise contacting the ductal epithelium with a cytokine or hematopoietic growth factor, such as GM-CSF.

DETAILED DESCRIPTION OF THE INVENTION

Figure 1:
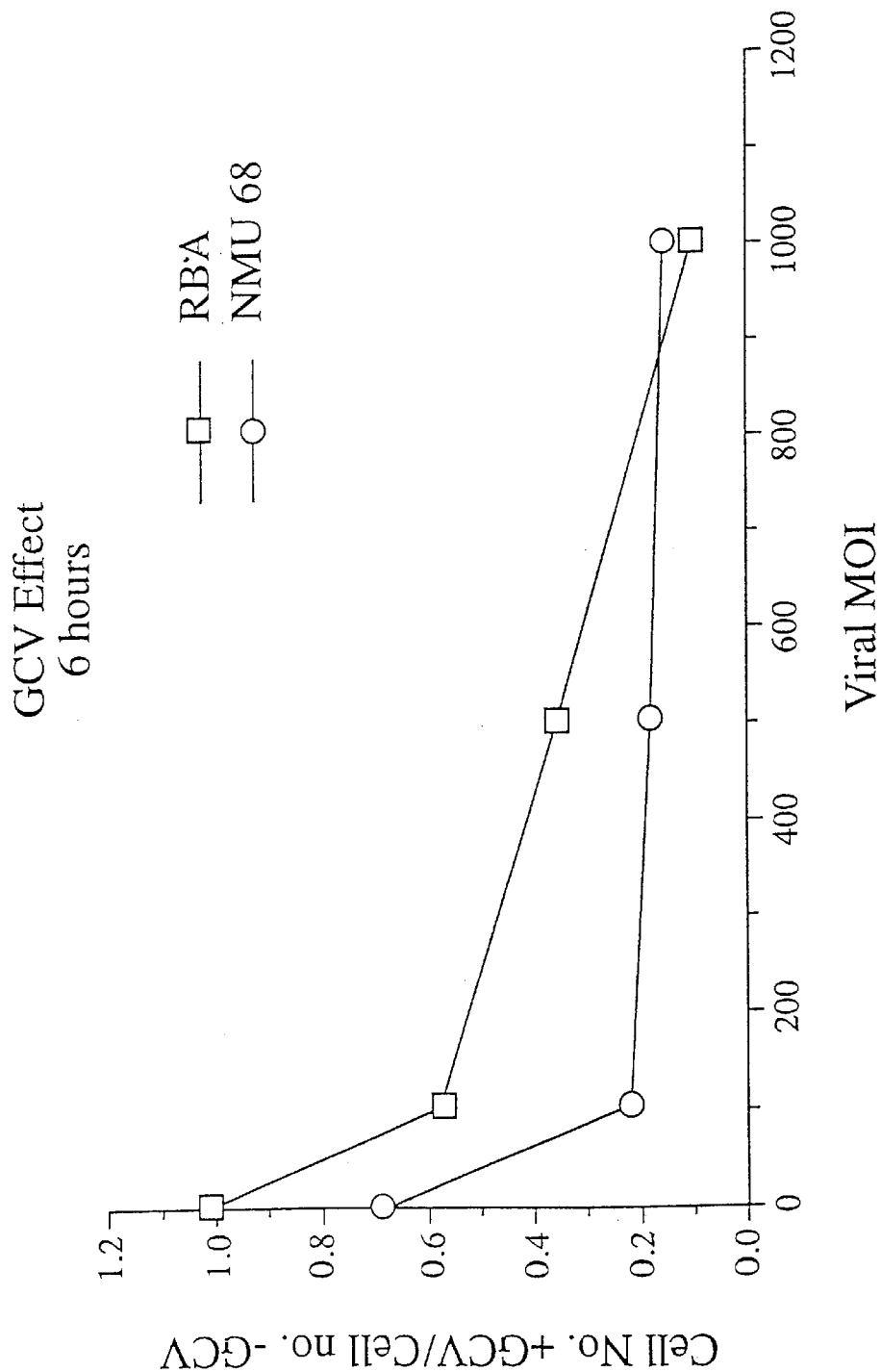
FIG. 1 is a graph of the ratio of cell no. in the presence of GCV over cell no. in the absence of GCV (Cell No.+GCV/Cell No.−GCV) versus viral multiplicity of infection (viral MOI), which shows the effect of the addition of 10 µg/ml GCV on NMU68 and RBA rat tumor cell lines 6 hrs after transduction with adenoviral-Herpes simplex thymidine kinase (AdHS-tk) at titers of 0, 100, 500 and 1,000 moi. After the cells were maintained in the presence of GCV for 3 days, they were counted using trypan blue exclusion as a measure of cell viability and cell numbers were normalized to the growth of cells in the absence of ganciclovir (GCV).

The present invention is based on the observation that the overwhelming majority of breast cancers arise from epithelial cells, particularly those epithelial cells which line the ducts of the mammary gland and are collectively referred to as the ductal epithelium. The present invention is also based on the exocrine nature of the mammary gland. Given that the mammary gland is an exocrine gland, it was further observed that the central canal or duct could provide a means of directly accessing the ductal epithelium for localized prophylactic and therapeutic treatment of cancer. Based on these observations, the prophylactic and therapeutic methods of the present invention were developed.

Prophylactic Method

The prophylactic method of the present invention is a method of treating the ductal epithelium of an exocrine gland prophylactically for a disease that affects the ductal epithelium of the exocrine gland. The method comprises contacting, preferably by ductal cannulation, the ductal epithelium of the exocrine gland with an epithelium-destroying agent so as to destroy cells of the ductal epithelium affected by the disease.

In one embodiment of the prophylactic method of the present invention, the ductal epithelium of a mammary gland is treated prophylactically for cancer so as to inhibit the formation of cancer of ductal epithelial origin. The method comprises contacting, preferably by ductal cannulation, the ductal epithelium of the mammary gland with an epithelium-destroying agent. The agent preferably is a vector comprising a thymidine kinase gene, such as a Herpes simplex thymidine kinase gene, and ganciclovir, a vector comprising a HPRT gene and HAT nucleotide, a cytolytic virus, such as a Vaccinia virus, or ethanol. The method can additionally comprise contacting the ductal epithelium with a cytokine or hematopoietic growth factor, such as GM-CSF.

In another embodiment of the prophylactic method of the present invention, the ductal epithelium of an exocrine gland, such as a mammary gland, is treated prophylactically for cancer so as to inhibit the formation of cancer of ductal epithelial origin. The method comprises contacting, preferably by ductal cannulation, the ductal epithelium of the exocrine gland with an epithelium-destroying agent to destroy less than all of the ductal epithelium so as to inhibit the formation of cancer of ductal epithelial origin. Preferably, up to about 70%, 80%, 85%, 90% or 95% of the ductal epithelium is destroyed.

The epithelium-destroying agent is preferably a vector comprising a thymidine kinase gene, such as that from Herpes simplex, and ganciclovir, which can be brought into contact with the ductal epithelium by any suitable means, preferably by ductal cannulation or by systemic administration, a vector comprising a HPRT gene and HAT nucleotide, which can be brought into contact with the ductal epithelium by any suitable means, preferably by ductal cannulation or by systemic administration, a vector comprising a gene, which upon transformation of a cell of the ductal epithelium and expression therein, induces apoptosis or death of the transformed cell, such as bclxs, ethanol, or a cytolytic virus, such as Vaccinia virus.

The above method can additionally comprise the administration of a cytokine or hematopoietic growth factor, such as GM-CSF. The GM-CSF can be brought into contact with the ductal epithelium of the mammary gland by any suitable means, such as by ductal cannulation of GM-CSF or a vector comprising a gene encoding GM-CSF, in which case the vector can be the same vector as the one encoding the thymidine kinase, HPRT or apoptosis-inducing gene, or it can be systemically administered.

This embodiment of the prophylactic method can be used to treat any exocrine gland. However, it is particularly useful in the treatment of the mammary gland.

The above-described prophylactic method of treating a mammary gland is particularly useful in treating a mammary gland in a mammal at risk for developing breast cancer. The mammary gland can be characterized as one that has never had a tumor, one that had a tumor previously but the tumor is no longer detectable due to other prior therapeutic treatment, or one that has an incipient or occult tumor, preneoplasia or ductal hyperplasia. Normally, hyperplasias and incipient and occult tumors are not detectable by means of physical examination or radiography. Accordingly, the prophylactic method will find use in cases where there is reason to take some prophylactic measures, such as when there are known inherited factors predisposing to cancers, where there are suspicious lesions present in a breast with the potential for developing into a malignancy, where there has been exposure to carcinogenic agents in the environment, where age predisposes to a cancer, where cancer of another gland, e.g., the mammary gland of the contralateral breast, suggests a propensity for developing cancer, or where there is a fear or suspicion of metastasis.

Therapeutic Method

The therapeutic method of the present invention is a method of treating the ductal epithelium of an exocrine gland therapeutically for a disease that affects the ductal epithelium of the exocrine gland. The method comprises contacting, preferably by ductal cannulation, the ductal epithelium of the exocrine gland with an epithelium-destroying agent so as to destroy cells of the ductal epithelium affected by the disease.

In one embodiment of the therapeutic method of the present invention, the ductal epithelium of a mammary gland is locally treated therapeutically for cancer so as to destroy cancerous and noncancerous cells of the ductal epithelium and inhibit the spread of cancer. The method comprises contacting, preferably by ductal cannulation, the ductal epithelium of the mammary gland with an epithelium-destroying agent, which need not, and preferably does not, specifically target cancerous cells. The agent preferably is a vector comprising a thymidine kinase gene, such as a Herpes simplex thymidine kinase gene, and ganciclovir, a vector comprising a HPRT gene and HAT nucleotide, a cytolytic virus, such as a Vaccinia virus, or ethanol. The method can additionally comprise contacting the ductal epithelium with a cytokine or hematopoietic growth factor, such as GM-CSF.

In the therapeutic method, the epithelial-destroying agent should destroy all of the diseased or malignant epithelium. In addition, the ductal epithelium immediately surrounding the diseased/malignant epithelium also preferably should be destroyed.

Combined Therapeutic/Prophylactic Method

The present invention also provides a method of treating the ductal epithelium of a mammary gland both therapeutically and prophylactically for cancer. The method comprises treating the mammary gland therapeutically with any given therapeutic method, such as those currently known and used in the art. Examples of such methods include surgical removal of the cancerous tissue, radiation therapy and chemotherapy. The method further comprises contacting, either concomitantly with or subsequently to the therapeutic treatment, the ductal epithelium of the mammary gland, e.g., by ductal cannulation, with an epithelium-destroying agent, which preferably does not specifically target cancerous cells, so as to destroy any remaining cancerous cells and noncancerous cells and inhibit the spread of cancer. The epithelium-destroying agent is preferably a vector comprising a thymidine kinase gene, such as a Herpes simplex thymidine kinase gene, combined with ganciclovir, a vector comprising a HPRT gene combined with HAT nucleotide, a cytolytic virus, such as a Vaccinia virus, or ethanol. The method can additionally comprise contacting the ductal epithelium with a cytokine or hematopoietic growth factor, such as GM-CSF.

Alternative Embodiments of Prophylactic & Therapeutic Methods

Although preferred embodiments have been described above, the methods of the present invention can be used to treat the ductal epithelium of any exocrine gland. Examples of exocrine glands, other than the mammary gland, which can be treated with the present inventive methods include, among others, the prostate, liver, gall bladder, pancreas, kidneys, sweat glands, and salivary glands. The methods are especially useful in the prophylactic and therapeutic treatment of the ductal epithelium of mammary glands.

Similarly, the methods can be used to treat an exocrine gland for any disease that affects the exocrine ductal epithelium. The methods are particularly useful in the treatment of cancer, including the stages of hyperplasia, adenoma, carcinoma in situ, and carcinoma, of ductal epithelial origin.

Any method can be used to destroy the ductal epithelium. It is preferred, however, that the destruction is limited to the ductal epithelium or a part thereof.

Any method of contacting the ductal epithelium can be used to effect local treatment. Preferably, ductal cannulation is used. Although any duct or lobule can be cannulated, it is preferred that the central canal or duct be cannulated. Ductal cannulation also enables direct injection of a tumor mass, if desired.

Any epithelium-destroying agent can be used to destroy the ductal epithelium of an exocrine gland. The agent preferably should not destroy cells other than cells of the ductal epithelium and preferably should not result in side effects, the adversity of which outweigh the benefits of destruction of the ductal epithelium. In no event should the methods be used to destroy completely the ductal epithelium of an exocrine gland in the prophylactic/therapeutic treatment of a given disease, wherein the complete destruction of the ductal epithelium, in and of itself, would result in death of the mammal so treated.

Examples of agents that can be used in the context of the prophylactic and therapeutic methods of the present invention include cytotoxic agents. Any cytotoxic agent known in the art and suitable for contacting the ductal epithelium of an exocrine gland of a mammal can be used. In addition to ethanol and GCV described above, other examples of cytotoxic agents and their prodrugs include genistein, okadaic acid, 1-β-D-arabinofuranosyl-cytosine, arabinofuranosyl-5-aza-cytosine, cisplatin, carboplatin, actinomycin D, asparaginase, bis-chloro-ethyl-nitroso-urea, bleomycin, chlorambucil, cyclohexyl-chloro-ethyl-nitroso-urea, cytosine arabinoside, daunomycin, etoposide, hydroxyurea, melphalan, mercaptopurine, mitomycin C, nitrogen mustard, procarbazine, teniposide, thioguanine, thiotepa, vincristine, 5-fluorouracil, 5-fluorocytosine, adriamycin, cyclophosphamide, methotrexate, vinblastine, doxorubicin, leucovorin, taxol, anti-estrogen agents such as tamoxifen, intracellular antibodies against oncogenes, the flavonol quercetin, Guan-mu-tong extract, retinoids such as fenretinide, nontoxid retinoid analogues such as N-(4-hydroxyphenyl)-retinamide (HPR), and monoterpenes such as limonene, perillyl alcohol and sobrerol. Preferably, the agent is locally administered, especially if administration of the agent is accompanied by toxic side effects. Otherwise, the agent can be administered by any suitable route, such as systemic administration.

A cytolytic virus also can be used as an agent. Any cytolytic virus can be used as long as the organism mounts a rapid immunological response to it such that the virus cannot cause disease if it escapes the ductal epithelium. Examples of cytolytic viruses include Vaccinia viruses and Sindbis viruses, which can also be used as vectors. Preferably, a Vaccinia virus is used. Due to lack of mucosal immunity, Vaccinia infectious particles enter and lyse the breast epithelial cells, yet stromal immunity destroys the particles as soon as they leave the ductile tree of the exocrine gland, thereby preventing cytolysis beyond the ductal epithelium. The advantages of Vaccinia administration are that it eliminates the need for high titer virus, the need to induce cell division in the breast, and the need to administer a drug to effect cell death.

A vector comprising a suicide gene also can be used as an agent, in conjunction with an agent that destroys the ductal epithelium of an exocrine gland. The vector comprising a suicide gene, upon transformation of a cell of the ductal epithelium and expression therein, renders the transformed cell sensitive to the epithelium-destroying agent, increases the sensitivity of the transformed cell to the agent, converts the agent from a prodrug to an active drug, activates the conversion of the agent from a prodrug to an active drug, enhances the effect of the agent or, itself, produces a protein that is cytotoxic. A preferred suicide gene for use in the present inventive methods is the one described above, i.e., a thymidine kinase, such as the one from Herpes simplex, which phosphorylates GCV, which, in turn, inhibits DNA replication. Another example of a suicide gene is cytosine deaminase, which is used in conjunction with 5-fluorocytosine. If the vector comprising the suicide gene is administered locally to the ducts, the cytotoxic agent or precursor can be administered systemically, since only transfected cells will be affected. In this regard, the bystander effect, i.e., the death of neighboring uninfected cells, presumably due to transfer of toxic byproducts through gap junctions between cells in the same compartment, obviates the need for every cell in the ductal epithelium, which is to be destroyed, to be infected. However, sufficient time must be allowed between contacting the ductal epithelium with the suicide gene and the prodrug, for example, to achieve efficient killing of the breast epithelial cells.

A vector comprising an apoptosis-inducing gene also can be used as an agent that destroys the ductal epithelium of an exocrine gland (Vaux, Cell 76: 777–779 (1994)). Examples of apoptosis-inducing genes include ced genes, myc genes (overexpressed), the bclxs gene, the bax gene, and the bak gene. The apoptosis-inducing gene causes death of transfected cells, i.e., by inducing programmed cell death. For example, the bclxs gene, bax gene, or bak gene can be used to inhibit bcl-2 or bcl-$x_L$, leading to apoptosis. Where necessary, a vector comprising an apoptosis-inducing gene can be used in combination with an agent that inactivates apoptosis inhibitors such as bcl-z, p35, IAP, NAIP, DAD1 and A20 proteins.

Suicide and apopotosis genes can be administered by way of a viral vector, such as an adenoviral or retroviral vector. Adenoviral vectors enable the generation of high titer recombinant viruses ($10^{11}$/ml) and the efficient transduction of postmitotic cells because adenoviral DNA exists as an episome in the nucleus (Verma, Molecular Medicine 1: 2–3 (1994)).

According to one preferred embodiment, the gene can be under the transcriptional regulation of a Rous sarcoma viral promoter. Alternatively, it can be under the control of an epithelial tissue-specific or cell-specific promoter.

Uptake of recombinant virus can be facilitated by pretreatment or simultaneous treatment with polybrene or, for example, in the case of a retrovirus, attachment of the functional fragment of an antibody to the viral particle.

In another embodiment, the apoptosis gene or suicide gene can be present in a recombinant microorganism, which will express the gene. One particularly preferred microorganism for this purpose is the bacterium *Listeria monocytogenes*.

Other methods known in the art for introduction of raw DNA into cells can be used in the methods of the present invention. Alternatively, liposomes, complexes between polypeptide ligands for receptors on mammary ductal epithelial cells, including complexes of antibodies and functional fragments thereof, and plasmids can be used (Mulligan, Science 260: 926–931 (1993)). Epithelial cell-specific promoters, such as whey acidic protein (wap), can be used to target expression of a given gene, e.g., a suicide gene, in ductal epithelial cells. Use can also be made of wild-type tumor suppressor genes, such as p53 or Mcs-1 (rat), homeobox genes expressed in normal cells but not in cancerous cells, and the maspin gene.

Additionally, the ductal epithelium can be contacted with an agent to effect the scavenging of epithelial cells destroyed in accordance with the present invention, e.g., a cytokine/growth factor. Suitable cytokines/growth factors include GM-CSF, G-CSF, IL-2, IL-4, IL-6, IL-7, hCG, TNF-α, INF-α and INF-γ. Such factors can be contacted with the ductal epithelium directly or by expression of a vector comprising a gene encoding the factor, in which case the vector can be the same one that comprises a suicide gene, for example. The factors stimulate a potent, long-lasting, and specific cell immunity, requiring both CD4 and CD8 cells. The immune response is designed to scavenge destroyed ductal epithelial cells by generating autoimmunity towards epithelial cell antigens.

The ductal epithelium is preferably contacted with the agent by introduction of the agent through the central canal or duct of the exocrine ductal epithelium, such as by ductal cannulation. However, in the case of the mammary gland, for example, there are 6–9 major ducts that emanate from the nipple and serially branch into other ducts, terminating in lobulo-alveolar structures (Russo et al. (1990), supra): Accordingly, in some circumstances, such as those in which even more localized treatment is necessary or desired, for example, by the choice of anti-cancer agent, it may be preferable to contact the ductal epithelium of the exocrine gland through one of the other ducts or through a lobulo-alveolar structure as opposed to the central canal or duct. In this regard, ductal cannulation enables intratumoral injection.

The methods of the present invention can be combined with other methods of prophylactic and therapeutic treatment in addition to those cited above, such as methods that target destruction of cancer cells, e.g., by targeting of cell-surface markers, receptor ligands, e.g., ligands to gastrin-releasing peptide-like receptors, tumor-associated antigens, e.g., the 57 kD cytokeratin or the antigen recognized by the monoclonal antibody GB24, the extracellular matrix glycoprotein tamascin, antisense oncogenes such as c-fos, homeobox genes that are expressed in cancer cells but not normal cells, tumor-infiltrating lymphocytes that express cytokines, RGD-containing peptides and proteins, which are administered following surgery, lipophilic drug-containing liposomes to which are covalently conjugated monoclonal antibodies for targeting to cancer cells, low fat diet, moderate physical exercise and hormonal modulation. For prostate cancer, anti-testosterone agents can be used as well as an inhibitor of cell proliferation produced by prostatic stromal cells and C-CAM, an epithelial cell adhesion molecule.

The following examples are presented to illustrate the present invention, not to limit its scope. The examples make use of the rat mammary tumor model, which has been deemed an appropriate experimental model for understanding breast cancer in humans (Sukumar et al., Mutation Res. 333 (1–2): 37–44 (1995); Russo et al., supra). In fact, 90–100% of female rats develop mammary tumors in this model when they are administered the carcinogen NMU at 55 days of age (Sukumar, Cancer Cells 4: 199–204 (1990)).

EXAMPLES

Example 1

This example demonstrates the successful delivery of virus and other agents into the mammary ductile tree by a single injection through the teat.

ADV/CMV-β-gal (from Dr. William Burns, Johns Hopkins University) is an adenoviral 5 vector constructed with a β-galactosidase gene controlled by a cytomegaloviral promoter. It was delivered into the mammary gland by injection of a viral suspension in 20 μl of 0.2% trypan blue in Tris buffer through the teat of a rat. The nipple was extruded, and the sphincter removed by excising the nipple. In the rat, the muscle prevents fluid from regurgitating into the breast and had to be excised in order to visualize the ductal opening and administer the agent. Trypan blue was used as a tracking dye to ensure correct delivery to the ductile tree. Injection about 30 days postpartum resulted in the mammary epithelial tree being clearly visible. Ethyl alcohol (70%) was also successfully delivered by a single injection through the teat.

Example 2

This example demonstrates that adenovirus can efficiently transduce human mammary epichelial cells in vitro.

ADV/CMV-β-gal was used to transduce HBL100 mammary epithelial cells in vitro. The β-gal enzyme in this construct contains a nuclear localization signal and results in dense nuclear staining.—HBL100 cells ($10^2$) were plated in 24-well plates, and transduced with virus at various doses and stained with X-gal 48 hrs later. Essentially all cells were infected at a moi=$10^4$.

This experiment also has been performed in human mammary tumor cells MCF-7 (American Type Culture Collection (ATCC), Rockville, Md.), human mammary epithelial cells MCF-10A (ATCC), and two rat mammary cancer cell lines, RBA (from Dr. Leonard Cohen) and 37-2 (from Dr. C. Marcelo Aldaz) with the same results. More efficient adenoviral constructs have been used, thereby achieving 100% infection at a moi=$10^3$. These experiments demonstrate successful infection by and expression of adenovirus carrying the lacZ indicator gene, which permits staining the cells blue by the expression of the enzyme β-galactosidase.

Example 3

This example demonstrates that infection with an AdHS-tk construct followed by GCV treatment effectively kills mammary tumor cells in vitro.

RBA and NMU68 are two rat mammary tumor cell lines derived from a DMBA- and a NMU-induced tumor, respectively [DMBA=dimethylbenz[a]anthracene, NMU=N'-nitro N'-methylurea]. Each cell line was plated at a density of $5 \times 10^2$ in 48-well plates (1.1 cm) and allowed to settle overnight. The next morning, they were transduced with AdHS-tk (Chen et al., PNAS(USA) 91: 3054–57 (1994); obtained from S. Woo and E. Aguilar-Cordova, Baylor College of Medicine, Houston, Tex.) at titers of 0, 100, 500, and 1000 moi, and then, 6 hrs later, GCV (10 μg/ml) was added to the culture media. The cells were maintained in the presence of GCV for 3 days and then counted using trypan blue exclusion as a measure of cell viability. The cell numbers were normalized to the growth of cells in the absence of GCV. The results are shown in FIG. 1. More than 80% of the cells of each cell line were killed at a moi of $10^3$.

Example 4

This example demonstrates the prophylactic effect of the method of the present invention.

The mammary glands (6 on each side) of six virgin 50 day old Sprague Dawley rats were injected with AdHS-tk on the left side and trypan blue on the right side or left untreated. One rat remained completely untreated with the virus or GCV and served as a positive control for NMU-induced tumorigenesis. On the day of surgery, rats were given an intramuscular injection of 5 μg estradiol valerate and were anesthetized with an isofluorane/$O_2$ mixture. The nipples were cannulated with a 33 gauge needle. Twenty μl of AdHS-tk diluted in trypan blue carrier (1 mM $MgCl_2$, 20 μg/ml polybrene in 10% glycerol, 0.4% trypan blue in saline) at a concentration of $5 \times 10^7$ particles/μl were injected into the duct. Carrier control mammary glands received 20 μl of trypan blue carrier alone. An animal was considered treated when at least three glands were successfully injected with trypan blue and another three glands were successfully injected with AdHS-tk. The remaining glands were left untreated. Twelve hrs later, the rats were injected with 125 mg/kg body weight GCV twice daily for three days. The rats were then given a second intramuscular injection of 5 μg estradiol valerate and intraperitoneal injections of 100 μg/kg body weight GCV once daily for three days. Five to seven days after GCV treatment, the rats were given an intravenous injection of NMU dissolved in 0.05% acetic acid (Ash Stevens, Colo.; 50 mg NMU/kg body weight) and were subsequently monitored for general health and the appearance of tumors at weekly intervals for 8 months. The results were as follows:

| Treatment | No. of Tumors | No. of Total Glands | % of Glands with Tumor |
|---|---|---|---|
| Untreated Control | 5 | 12 | 41.7 |
| Trypan Blue and Ganciclovir | 5 | 17 | 29.4 |
| No injection; Ganciclovir | 5 | 20 | 25.0 |
| AdHS-tk and Ganciclovir | 2* | 35 | 5.7 |

(*) The two tumors (size <5 mm) in this group were detected during necropsy at the termination of the experiment 8 months later. The difference between tumors appearing in treated versus control glands was significant by $Chi^2$ analysis (p<0.01)

The above results show that the method of the present invention inhibits the formation of cancer of ductal epithelial origin in this rat model, in which NMU induces the formation of mammary tumors in 90–100% of female rats of similar age. Surprisingly and unexpectedly, this prophylactic effect was achieved without extensive destruction of the mammary glands. These data demonstrate that selective destruction of epithelial cells, e.g., key stem cells, can be sufficient to provide prophylactic protection against carcinogen-induced tumor formation in the ductal epithelium of the mammary gland.

Example 5

This example demonstrates the efficient transfection of mammary epithelial cells in vivo.

Lytic Vaccinia virus ($10^6$ Vaccinia-HA, which also carries lacZ, in 20 μl 0.2% trypan blue) was injected into the mammary glands through the teat of 45 day old virgin rats. Contralateral control glands were injected with 0.2% trypan blue. The glands were excised after 3 days. Frozen mammary gland sections were stained with X-gal and counterstained with eosin. When Vaccinia-HA was injected via the rat teat, it was able to infect the epithelial cells. At 3 days post-infection, the X-gal staining was confined primarily to the epithelial cells.

Example 6

This example demonstrates the cytotoxicity of Vaccinia/HA on HBL100 cells in vitro.

HBL100 cells (from ATCC, Rockville, Md.) were plated in DME:F12 medium (50% Dulbecco's Modified Eagles Medium: 50% Ham's F12 Supplement) containing 10% fetal bovine serum and 10 μg/ml insulin at a density of $5 \times 10^4$ cells/well and incubated at 37° C. overnight. Vaccinia/HA, at concentrations of 0 moi, 0.1 moi, or 1.0 moi, was added to the culture medium, and the cells were incubated at 37° C. for at least 3 days. More than 90% of the cells were dead within 72 hrs of infection at 0.1 moi.

Example 7

This example shows the death of rat mammary tumor cells in culture by infection with Vaccinia/HA.

Cells of rat mammary cancer cell line RBA were plated in growth medium at a density of $5 \times 10^4$ cells/well and incubated at 37° C. overnight. Vaccinia virus engineered to express β-galactosidase and hemagglutinin genes (Vaccinia/HA) was added to the culture medium at concentrations of 0 moi, 0.1 moi, or 1.0 moi and incubated at 37° C. for at least 3 days. Up to 90% of the cells were lysed within 72 hours of injection at 1.0 moi.

Example 8

This example demonstrates the destruction of mammary epithelium by transfection with Vaccinia/HA in vivo.

The mammary glands of 45-day old virgin rats were injected through the teat with $1\times10^7$ particles of Vaccinia/HA in 20 $\mu$l 0.2% trypan blue (tracking dye). Contralateral control glands were injected with 0.2% trypan blue. The glands were excised after 3 days, fixed in chloroform:methanol:acetic acid and stained in iron-hematoxylin. Branching structures of a whole-mounted mammary gland injected with tracking dye alone were visible up to the end buds and alveoli. Also visible as brown bodies were the mammary lymph nodes. Examination of a whole-mounted mammary gland of the same rat receiving Vaccinia/HA in trypan blue on the contralateral side revealed that only about 30% of the ducts remained. In addition, the lymph nodes were considerably enlarged, denoting the mounting of an immune response to clear the Vaccinia from the vicinity.

All publications, patents, and patent applications cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A method of treating the ductal epithelium of a mammary gland therapeutically for cancer, which method consists of contacting, by ductal cannulation, the ductal epithelium of the mammary gland with a composition consisting of one or more cytotoxic compounds to destroy the ductal epithelium so as to inhibit the spread of cancer.

2. The method of claim 1, wherein said cytotoxic compound is an anti-estrogen agent.

3. The method of claim 2, wherein said anti-estrogen agent is tamoxifen.

4. A method of treating the ductal epithelium of a mammary gland therapeutically for cancer, which method consists of contacting, by ductal cannulation, the ductal epithelium of the mammary gland with a composition consisting of (i) one or more cytotoxic compounds and (ii) a cytokine or hematopoietic growth factor to destroy the ductal epithelium so as to inhibit the spread of cancer.

5. The method of claim 4, wherein said hematopoietic growth factor is GM-CSF.

6. The method of claim 5, wherein said cytotoxic agent is an anti-estrogen agent.

7. The method of claim 6, wherein said anti-estrogen agent is tamoxifen.

8. The method of claim 4, wherein said cytotoxic compound is an anti-estrogen agent.

9. The method of claim 8, wherein said anti-estrogen agent is tamoxifen.

10. A method of treating the ductal epithelium of a mammary gland therapeutically for cancer, which method comprises contacting, by ductal cannulation, the ductal epithelium of the mammary gland with a cytotoxic agent to destroy only the ductal epithelium so as to inhibit the spread of cancer.

11. The method of claim 10, wherein said cytotoxic agent is an anti-estrogen agent.

12. The method of claim 11, wherein said anti-estrogen agent is tamoxifen.

13. A method of treating the ductal epithelium of a mammary gland therapeutically for cancer, which method comprises contacting, by ductal cannulation, the ductal epithelium of the mammary gland with (i) a cytotoxic agent and (ii) a cytokine or hematopoietic growth factor to destroy only the ductal epithelium so as to inhibit the spread of cancer.

14. The method of claim 13, wherein said hematopoietic growth factor is GM-CSF.

15. The method of claim 14, wherein said cytotoxic agent is an anti-estrogen agent.

16. The method of claim 15, wherein said anti-estrogen agent is tamoxifen.

17. The method of claim 13, wherein said cytotoxic agent is an anti-estrogen agent.

18. The method of claim 17, wherein said anti-estrogen agent is tamoxifen.

* * * * *